United States Patent

Iwasawa et al.

Patent Number: 5,220,028
Date of Patent: Jun. 15, 1993

[54] HALOGENO-4-METHYLPYRAZOLES

[75] Inventors: Yoshihiro Iwasawa; Susumu Yamamoto; Kenji Suzuki; Hiroshi Murakami; Fumio Suzuki, all of Funabashi, Japan

[73] Assignee: Nissan Chemical Industries, Ltd., Tokyo, Japan

[21] Appl. No.: 869,046

[22] Filed: Apr. 14, 1992

Related U.S. Application Data

[63] Continuation of Ser. No. 421,987, Oct. 16, 1989, abandoned.

Foreign Application Priority Data

Oct. 27, 1988 [JP] Japan .................. 63-271438

[51] Int. Cl.⁵ .................. C07D 401/04; C07D 231/16
[52] U.S. Cl. .................. 546/279; 548/364.1; 548/373.1
[58] Field of Search .................. 548/375, 376, 364.1, 548/373.1; 546/279

[56] References Cited

U.S. PATENT DOCUMENTS

| | | | |
|---|---|---|---|
| 4,668,277 | 5/1987 | Yamamoto et al. | 71/92 |
| 4,752,326 | 6/1988 | Ohyama et al. | 548/375 |
| 4,826,867 | 5/1989 | Jensen-Korte et al. | 548/375 |
| 4,954,164 | 9/1990 | Suzuki et al. | 71/92 |
| 5,053,517 | 10/1991 | Takigawa et al. | 548/376 |

OTHER PUBLICATIONS (1) Advances in Heterocyclic Chemistry, vol. 6, pp. 391-392 (1966).

(2) Comprehensive Heterocyclic Chemistry, vol. 5, pp. 239-240 (1984).

Primary Examiner—Patricia L. Morris
Attorney, Agent, or Firm—Frishauf, Holtz, Goodman & Woodward

[57] ABSTRACT

There are disclosed halogeno-4-methylpyrazoles represented by the formula (I):

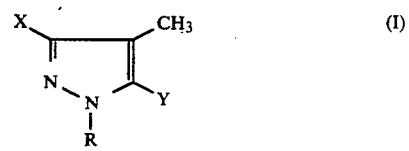

wherein R represents an alkyl group having 1 to 4 carbon atoms, a substituted or unsubstituted phenyl group or a substituted or unsubstituted pyridyl group; X represents a hydrogen atom or a halogen atom; and Y represents a halogen atom, and a process for preparing the same which comprises reacting 1-substituted-4-methylpyrazoles of the formula (II):

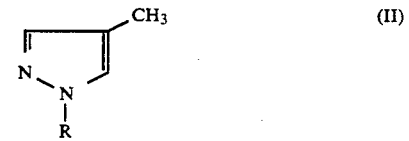

wherein R has the same meaning as defined above, with a halogen.

9 Claims, No Drawings

HALOGENO-4-METHYLPYRAZOLES

This application is a continuation of application Ser. No. 07/421,987, filed Oct. 16, 1989 (abandoned).

BACKGROUND OF THE INVENTION

This invention relates to halogeno-4-methylpyrazoles useful as intermediates for pharmaceuticals and agricultural chemicals, etc. and processes for producing the same, more particularly to 5-halogeno-1-substituted-4-methylpyrazoles and 3,5-dihalogeno-1-substituted-4-methylpyrazoles and processes for producing these.

Chemical Abstract vol. 71, 112859i discloses that no halogeno-methylpyrazole is formed, but a trimer is formed by bromination of 4-methylpyrazole.

Journal of Agricultural Food Chemistry (J. Agrc. Food. Chem.), vol. 25, No. 4, p. 884 (1977) discloses a process for preparing 4-methyl-3,5-dibromopyrazole which comprises permitting butyl lithium to act on 3,4,5-tribromopyrazole, followed by substitution with methyl iodide.

However, this process cannot be said to be an industrial production process, because synthesis of 3,4,5-tribromopyrazole is complicated, and moreover the synthesis steps are lengthy, and yet expensive butyl lithium is used.

Chemical Abstract Vol. 66, 94950x discloses a process for preparing 3-bromo-1,4-dimethylpyrazole which comprises brominating 1,4-dimethyl-5-hydroxycarbonylpyrazole, followed by decarboxylation.

However, this process cannot be said to be an industrial production process, because 1,4-dimethyl-5-carboxypyrazole is expensive, and the synthesis steps are complicated.

SUMMARY OF THE INVENTION

The present inventors have investigated intensively about processes for obtaining halogeno-4-methylpyrazoles with good yield, and consequently accomplished the present invention.

More specifically, the present invention concerns halogeno-4-methylpyrazoles represented by the formula (I):

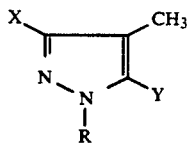

(wherein R represents an alkyl group having 1 to 4 carbon atoms, a substituted or unsubstituted phenyl group or a substituted or unsubstituted pyridyl group, X represents a hydrogen atom or a halogen atom and Y represents a halogen atom) and a process for preparing halogeno-4-methylpyrazoles represented by the formula (I), which comprises reacting 1-substituted-4-methylpyrazoles of the formula (II):

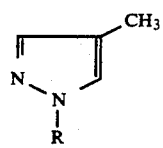

(wherein R represents an alkyl group having 1 to 4 carbon atoms, a substituted or unsubstituted phenyl group or a substituted or unsubstituted pyridyl group) with a halogen.

In the halogeno-4-methylpyrazoles of the above formula (I) and the 1-substituted-4-methylpyrazoles of the formula (II), the alkyl group of R having 1 to 4 carbon atoms may include a methyl group, an ethyl group, a n-propyl group, an i-propyl group, a n-butyl group, an i-butyl group, a t-butyl groups.

Examples of the substituted or unsubstituted phenyl group may include a phenyl group, a 2-methylphenyl group, a 3-methylphenyl group, a 4-methylphenyl group, a 2-ethylphenyl group, a 3-ethylphenyl group, a 4-ethylphenyl group, a 2-n-propylphenyl group, a 2-i-propylphenyl group, a 3-n-propylphenyl group, a 3-i-propylphenyl group, a 4-n-propylphenyl group, a 4-i-propylphenyl group, a 2-t-butylphenyl group, a 4-n-butylphenyl group, a 4-i-butylphenyl group, a 4-t-butylphenyl group, a 2,4-dimethylphenyl group, a 2,6-dimethylphenyl group, a 2,4-diethylphenyl group, a 2,6-diethylphenyl group, a 2-methoxyphenyl group, a 3-methoxyphenyl group, a 4-methoxyphenyl group, a 2-ethoxyphenyl group, a 3-ethoxyphenyl group, a 4-ethoxyphenyl group, a 2-n-propoxyphenyl group, a 2-i-propoxyphenyl group, a 3-n-propoxyphenyl group, a 4-n-propoxyphenyl group, a 4-i-propoxyphenyl group, a 2-n-butoxyphenyl group, a 4-n-butoxyphenyl group, a 4-i-butoxyphenyl group, a 4-t-butoxyphenyl group, a 2-chlorophenyl group, a 3-chlorophenyl group, a 4-chlorophenyl group, a 2-fluorophenyl group, a 3-fluorophenyl group, a 4-fluorophenyl group, a 2,4-dichlorophenyl group, a 2,4-difluorophenyl group, a 2,6-dichlorophenyl group, a 2,6-difluorophenyl group, a 2-nitrophenyl group, a 3-nitrophenyl group, a 4-nitrophenyl group, a 2-difluoromethoxyphenyl group, a 3-difluoromethoxyphenyl group, a 4-difluoromethoxyphenyl group, and the like, and examples of the substituted or unsubstituted pyridyl group may include a 2-pyridyl group, a 3-methyl-2-pyridyl group, a 4-methyl-2-pyridyl group, a 5-methyl-2-pyridyl group, a 6-methyl-2-pyridyl group, a 3-chloro-2-pyridyl group, a 4-chloro-2-pyridyl group, a 5-chloro-2-pyridyl group, a 6-chloro-2-pyridyl group, a 3,5-dichloro-2-pyridyl group, a 3-trifluoromethyl-2-pyridyl group, a 5-trifluoromethyl-2-pyridyl group, a 3-pyridyl group, a 2-methyl-3-pyridyl group, a 4-methyl-3-pyridyl group, a 5-methyl-3-pyridyl group, a 6-methyl-3-pyridyl group, a 2-chloro-3-pyridyl group, a 5-chloro-3-pyridyl group, a 6-chloro-3-pyridyl group, a 4-pyridyl group, a 2-methyl-4-pyridyl group, a 3-methyl-4-pyridyl group, a 2-chloro-4-pyridyl group, a 3-chloro-4-pyridyl group and the like.

Specific examples of the halogeno-4-methylpyrazoles of the formula (I) may include 5-chloro-1,4-dimethylpyrazole, 5-bromo-1,4-dimethylpyrazole, 5-chloro-1-phenyl-4-methylpyrazole, 5-bromo-1-phenyl-4-methylpyrazole, 5-chloro-1-(2-pyridyl)-4-methylpyrazole, 5-chloro-1-(3-pyridyl)-4-methylpyrazole, 5-chloro-1-(4-pyridyl)-4-methylpyrazole, 3,5-dichloro-1,4-dimethylpyrazole, 3,5-dibromo-1,4-dimethylpyrazole, 3,5-dichloro-1-phenyl-4-methylpyrazole, 3,5-dibromo-1-phenyl-4-methylpyrazole, 3,5-dichloro-1-(2-pyridyl)-4-methylpyrazole, 3,5-dichloro-1-(3-pyridyl)-4-methylpyrazole, 3,5-dichloro-1-(4-pyridyl)-4-methylpyrazole, 3,5-dibromo-1-(2-pyridyl)-4-methylpyrazole, 3,5-dibromo-1-(3-pyridyl)-4-methylpyrazole, 3,5-dibromo-1-(4-pyridyl)-4-methylpyrazole, and the like.

Specific examples of the 1-substituted-4-methylpyrazoles of the formula (II) may include 1,4-dimethylpyrazole, 1-ethyl-4-methylpyrazole, 1-n-propyl-4-methylpyrazole, 1-i-propyl-4-methylpyrazole, 1-n-butyl-4-methylpyrazole, 1-i-butyl-4-methylpyrazole, 1-t-butyl-4-methylpyrazole, 1-phenyl-4-methylpyrazole, 1-(2-pyridyl)-4-methylpyrazole, 1-(3-pyridyl)-4-methylpyrazole, 1-(4-pyridyl)-4-methylpyrazole and the like (In the above, n means normal, i means iso and t means tertiary, respectively).

The 1-substituted-4-methylpyrazoles represented by the formula (II) can be produced with good yield by the reaction between 2,3-dichloro-2-methylpropanal and a substituted hydrazine (see Japanese Provisional Patent Publication No. 270345/1988).

In the halogeno-4-methylpyrazoles of the above formula (I), as the halogen atom of X and Y, a chlorine atom and a bromine atom may be employed.

In the following, the reaction conditions of the 1-substituted-4-methylpyrazoles of the formula (II) and halogen are to be described in detail.

As the reaction temperature, a range generally of $-10°$ to $100°$ C. is employed.

As the reaction time, a range generally of 5 minutes to 15 hours is employed.

The present invention can be practiced with no solvent, but a solvent can be also used.

As the solvent, there may be included halogenated aliphatic hydrocarbons such as methylene chloride, chloroform, carbon tetrachloride, dichloroethane, tetrachloroethane, etc., halo-substituted aromatic hydrocarbons such as chlorobenzene, dichlorobenzene, etc.

The above solvents can be also used as a mixture of two or more kinds.

As the solvent, one or more solvents selected from halogenated aliphatic hydrocarbon solvents such as dichloroethane, etc., halo-substituted aromatic hydrocarbons such as o-dichlorobenzene, etc. are particularly preferred.

An amount of the solvent used may be generally in the range of 0.1 to 20 parts by weight, preferably 1 to 10 parts by weight, based on 1 part by weight of the 1-substituted-4-methylpyrazoles of the formula (II). Also, the solvent may be used those which are commercially available, but if necessary, when the solvent is subjected to drying treatment with molecular sieves, etc., good results can be obtained.

As the halogen, chlorine and bromine may be mentioned. The halogen can be used either in liquid or gaseous state.

An amount of the halogen used may be generally in the range of 0.5 to 1.6 moles, preferably 0.8 to 1.33 moles, per one mole of the 1-substituted-4-methylpyrazoles of the formula (II), when producing 5-halogeno-1-substituted-4-methylpyrazoles which is monohalogeno-material among the compounds represented by the formula (I).

On the other hand, in the case of producing 3,5-dihalogeno-1-substituted-4-methylpyrazoles which is dihalogeno material among the compounds represented by the formula (I), an amount of the halogen may be generally in the range of 1.4 to 3.0 moles, preferably 1.8 to 2.5 moles, based on one mole of the 1-substituted-4-methylpyrazoles of the formula (II).

As the reaction method between the 1-substituted-4-methylpyrazoles represented by the formula (II) and halogen, there may be employed the reaction in which the reaction is carried out by blowing with gaseous state or adding dropwise a halogen into 1-substituted-4-methylpyrazoles represented by the formula (II), or the method in which the 1-substituted-4-methylpyrazoles represented by the formula (II) are added dropwise into halogen, etc.

After completion of the reaction, the halogeno-4-methylpyrazoles represented by the formula (I) can be isolated by direct distillation, etc., but if necessary, it can be also obtained with good results by removing almost all the parts of remaining halogen and by-produced hydrohalogenic acid in the reaction mixture by such operation as reducing pressure or blowing of nitrogen as a pretreatment, subsequently treatment with an alkaline aqueous solution such as sodium hydroxide, potassium hydroxide, etc. completely, and then purification such as distillation, etc.

As the halogenating agent, in addition to the above chlorine and bromine atoms, there may be also used, for example, sulfuryl chloride, sulfuryl bromide, N-chlorosuccinimide, N-bromosuccinimide, tert-butyl hypochloride, etc.

Also, the reaction can be carried out without using a deacidificating agent, but an organic base such as triethylamine, N,N-dimethylaniline, pyridine, etc. or an inorganic base such as sodium carbonate, potassium carbonate, sodium hydroxide, etc. may be used.

The reaction can be carried out without using a catalyst, but as the catalyst, a Lewis acid such as $BF_3$, $AlCl_3$, $FeCl_3$, $SbCl_5$, $SbCl_5$, etc., a metal halide such as $CuCl$, $CuCl_2$, etc., a metal such as iron, copper, etc., or a halogen such as iodine, etc. may be added thereto.

By the reaction of the 1-substituted-4-methylpyrazoles represented by the formula (II) and halogen, halogeno-4-methylpyrazoles represented by the formula (I) can be obtained easily at high yield.

The 5-halogeno-1-substituted-4-pyrazoles which are monohalogeno-material among halogeno-4-methylpyrazoles represented by the formula (I) can be oxidized at the methyl group at the 4-position to produce 5-halogeno-1-alkyl-4-alkoxycarbonylpyrazoles which are useful as the intermediate for herbicides (Japanese Provisional Patent Publication No. 122488/1984).

Also, the 3,5-dihalogeno-1-substituted-4-methylpyrazoles which are dihalogeno material among halogeno-4-methylpyrazoles represented by the formula (I) can be oxidized at the methyl group at the 4-position to produce 3,5-dihalogeno-4-alkoxycarbonylpyrazoles which are useful as the intermediate for herbicides (Japanese Provisional Patent Publication No. 208977/1985).

The present invention is described in detail below by referring to examples, by which the present invention is not limited at all.

EXAMPLE 1

Into a mixture of 19.3 g (0.2 mole) of 1,4-dimethylpyrazole and 96 g of 1,2-dichloroethane was blown 18.9 g (0.266 mole) of chlorine under stirring for one hour, while maintaining the reaction temperature at 25° to 35° C.

After completion of blowing, the temperature was returned to room temperature, and analyzed by liquid chromatography to find that 17.5 g of 5-chloro-1,4-dimethylpyrazole was contained.

The yield of 5-chloro-1,4-dimethylpyrazole was 67%.

The above reaction mixture was washed with 30 g of a 20% aqueous sodium hydroxide solution, and after evaporation of the solvent, distillation was carried out by use of Widmer to give 17 g of 5-chloro-1,4-dimethylpyrazole of a purity of 95% at a boiling point range of 100° to 110° C./120 mm Hg.

¹H-NMR (CDCl₃): δ1.97 (3H, s), 3.75 (3H, s), 7.3 (1H, s).

EXAMPLE 2

Into a mixture of 9.65 g (0.1 mole) of 1,4-dimethylpyrazole and 48 g of 1,2-dichloroethane was blown 15.6 g (0.22 mole) of chlorine under stirring for one hour, while maintaining the reaction temperature at 5° to 15° C.

After completion of blowing, the temperature was returned to room temperature, and analyzed by liquid chromatography to find that 14.4 g of 3,5-dichloro-1,4-dimethylpyrazole was contained.

The yield of 3,5-dichloro-1,4-dimethylpyrazole was 87%.

After evaporation of the solvent from the above reaction mixture, distillation was carried out to give 15.2 g of 3,5-dichloro-1,4-dimethylpyrazole of a purity of 90% at a boiling point range of 98° to 109° C./120 mmHg.

¹H-NMR (CDCl₃): δ1.9 (3H, s), 3.7 (3H, s).

EXAMPLE 3

Into a mixture of 3.1 g (0.0323 mole) of 1,4-dimethylpyrazole and 7 g of carbon tetrachloride was blown 7 g (0.097 mole) of chlorine under stirring for one hour, while maintaining the reaction temperature at 80° C.

After completion of blowing, the reaction temperature was returned to room temperature, and after evaporation of the solvent, distillation was carried out to give 3.6 g of 3,5-dichloro-1,4-dimethylpyrazole of a purity of 95% at a boiling point range of 98° to 109° C./20 mmHg.

The yield of 3,5-dichloro-1,4-dimethylpyrazole was found to be 64%.

EXAMPLES 4

Into a mixture of 9.65 g (0.1 mole) of 1,4-dimethylpyrazole, 0.5 g of iron powder and 60 g of 1,2-dichloroethane was added dropwise 48 g (0.3 mole) of bromine under stirring for one hour, while maintaining the reaction temperature at 10° to 35° C., and stirring was continued at 80° C. for 15 hours.

After completion of the reaction, bromine was removed under reduced pressure and the reaction mixture was neutralized with a 10% sodium hydroxide. Subsequently, insolubles were removed by filtration, washed with water and after evaporation of the solvent, distillation was carried out to give 9.3 g of 3,5-dibromo-1,4-dimethylpyrazole of a purity of 98% at a boiling point range of 124° to 128° C./20 mmHg.

The yield of 3,5-dibromo-1,4-dimethylpyrazole was found to be 36%.

¹ H-NMR (CDCl₃): δ1.95 (3H, s), 3.8 (3H, s).

EXAMPLE 5

Into a mixture of 2.5 g (0.0164 mole) of 4-methyl-1-phenylpyrazole and 20 g of 1,2-dichloroethane was blown 1.0 g (0.0141 mole) of chlorine under stirring for 15 minutes, while maintaining the reaction temperature at 20° to 25° C.

The reaction mixture was analyzed by gas chromatography and 1.3 g of 5-chloro-4-methyl-1-phenylpyrazole was found to be contained. The yield was 41%.

GC-MS: M/e: 192 (M+), 157 (M+ —Cl), 130, 89, 77.

Into the above reaction mixture was further blown 3.0 g (0.0423 mole) of chlorine under stirring for 45 minutes, while maintaining the reaction temperature at 30° to 35° C. After evaporation of the solvent, the residue was recrystallized with n-hexane to give 1.1 g of 3,5-dichloro-1-(4-chlorophenyl)-4-methylpyrazole having a melting point of 90° to 91.5° C.

The isolated yield of 3,5-dichloro-1-(4-chlorophenyl)-4-methylpyrazole was 26%.

¹H-NMR (CDCl₃): δ2.09 (3H, s), 7.56 (4H, s).

We claim:

1. A halogeno-4-methylpyrazole represented by the formula (I):

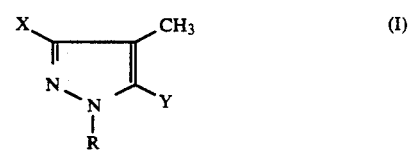

wherein R represents an alkyl group having 1 to 4 carbon atoms, or a substituted or unsubstituted pyridyl group wherein the substituents are methyl, halogen or trifluoromethyl; X represents a hydrogen atom or a halogen atom; and Y represents a halogen atom.

2. The halogeno-4-methylpyrazole according to claim 1, wherein R is an alkyl group having 1 to 4 carbon atoms, or an unsubstituted pyridyl group; X is a hydrogen atom, a chlorine atom or a bromine atom; and Y is a chlorine atom or a bromine atom.

3. The halogeno-4-methylpyrazole according to claim 1, wherein R is an alkyl group having 1 to 4 carbon atoms; X is a hydrogen atom, a chlorine atom or a bromine atom; and Y is a chlorine atom or a bromine atom.

4. The halogeno-4-methylpyrazole according to claim 1, wherein R is 2-pyridyl.

5. The halogeno-4-methylpyrazole according to claim 1, wherein R is the substituted pyridyl group.

6. The halogeno-4-methylpyrazole according to claim 1, wherein the substituted pyridyl group is a 3-methyl-2-pyridyl group, a 4-methyl-2-pyridyl group, a 5-methyl-2-pyridyl group, a 6-methyl-2-pyridyl group, a 3-chloro-2-pyridyl group, a 4-chloro-2-pyridyl group, a 5-chloro-2-pyridyl group, a 6-chloro-2-pyridyl group, a 3,5-dichloro-2-pyridyl group, a 3-trifluoromethyl-2-pyridyl group, a 5-trifluoromethyl-2-pyridyl group, a 3-pyridyl group, a 2-methyl-3-pyridyl group, a 4-methyl-3-pyridyl group, a 5-methyl-3-pyridyl group, a 6-methyl-3-pyridyl group, a 2-chloro-3-pyridyl group, a 5-chloro-3-pyridyl group, a 6-chloro-3-pyridyl group, a 4-pyridyl group, a 2-methyl-4-pyridyl group, a 3-methyl-4-pyridyl group, a 2-chloro-4-pyridyl group or a 3-chloro-4-pyridyl group.

7. The halogeno-4-methylpyrazole according to claim 1, selected from the group consisting of 5-chloro-1,4-dimethylpyrazole, 5-bromo-1,4-dimethylpyrazole, 5-chloro-1-(2-pyridyl)-4-methylpyrazole, 5-chloro-1-(3-pyridyl)-4-methylpyrazole, 5-chloro-1-(4-pyridyl)-4-methylpyrazole, 3,5-dichloro-1,4-dimethylpyrazole, 3,5-dibromo-1,4-dimethylpyrazole, 3,5-dichloro-1-(2-pyridyl)-4-methylpyrazole, 3,5-dichloro-1-(3-pyridyl)-4-methylpyrazole, 3,5-dichloro-1-(4-pyridyl)-4-methylpyrazole, 3,5-dibromo-1-(2-pyridyl)-4-methylpyrazole, 3,5-dibromo-1-(3-pyridyl)-4-methylpyrazole and 3,5-dibromo-1-(4-pyridyl)-4-methylpyrazole.

8. The halogeno-4-methylpyrazole according to claim 1, wherein R is a methyl group; X is a hydrogen atom; and Y is a chlorine atom.

9. The halogeno-4-methylpyrazole according to claim 1, wherein R is a methyl group; X is a chlorine atom; and Y is a chlorine atom.

* * * * *

UNITED STATES PATENT AND TRADEMARK OFFICE
CERTIFICATE OF CORRECTION

PATENT NO. : 5,220,028

DATED : June 15, 1993

INVENTOR(S) : IWASAWA et al

It is certified that error appears in the above-identified patent and that said Letters Patent is hereby corrected as shown below:

Column 6, line 37 (Claim 6): Delete "claim 1" and insert --claim 5--.

Signed and Sealed this

Twentieth Day of December, 1994

Attest:

BRUCE LEHMAN

*Attesting Officer*  *Commissioner of Patents and Trademarks*